(12) United States Patent
Kim et al.

(10) Patent No.: US 11,744,791 B2
(45) Date of Patent: Sep. 5, 2023

(54) COSMETIC COMPOSITION COMPRISING AMIDE-BASED COMPOUND

(71) Applicant: Neopharm Co., Ltd., Daejeon (KR)

(72) Inventors: Yoon Kim, Daejeon (KR); Kyung Sook Yoo, Daejeon (KR); Bu-Mahn Park, Daejeon (KR); Yu Ra Jung, Daejeon (KR); Hye Seong Shin, Daejeon (KR)

(73) Assignee: Neopharm Co., Ltd., Daejeon (KR)

( * ) Notice: Subject to any disclaimer, the term of this patent is extended or adjusted under 35 U.S.C. 154(b) by 69 days.

(21) Appl. No.: 17/198,783

(22) Filed: Mar. 11, 2021

(65) Prior Publication Data
US 2021/0283041 A1 Sep. 16, 2021

(30) Foreign Application Priority Data
Mar. 13, 2020 (KR) .......................... 10-2020-0031120

(51) Int. Cl.
*A61K 8/88* (2006.01)
*C12N 5/077* (2010.01)
(52) U.S. Cl.
CPC .............. *A61K 8/88* (2013.01); *C12N 5/0653* (2013.01)
(58) Field of Classification Search
CPC .................................. A61K 8/88; C12N 5/0653
See application file for complete search history.

(56) References Cited

FOREIGN PATENT DOCUMENTS

KR    19980053300 A  *  9/1998
KR    1020190040795     4/2019

OTHER PUBLICATIONS

Machine translation of KR 19980053300A from Google Patents (Year: 1998).*
Machine translation of KR 1020190040795 from Google Patents (Year: 2019).*
Purnamawati, S. et al., 2017, "The role of moisturizers in addressing various kinds of dermatitis: A review.", Clinical Medicine and Research, 15, 75-87. (Year: 2017).*
Narala, V. et al., 2014, "The role of nitrated fatty acids and peroxisome proliferator-activated receptor gamma in modulating inflammation", international immunopharmacology, 23, 283-287 (Year: 2014).*

* cited by examiner

*Primary Examiner* — Bethany P Barham
*Assistant Examiner* — Ayaan A Alam
(74) *Attorney, Agent, or Firm* — BLANK ROME LLP

(57) ABSTRACT

Provided are a cosmetic composition for promoting lipid biosynthesis, a cosmetic composition for inducing differentiation of adipose precursor cells or stem cells into adipocytes, and a cosmetic composition for moisturizing the skin, all of which include an amide-based compound. The cosmetic composition according to the present invention can promote the lipid biosynthesis and can promote expression of PPAR-γ and cluster of differentiation 44, which are markers for labeling human adipose tissue-derived stem cells, to promote differentiation of the adipose tissue-derived stem cells into mature adipocytes, thereby improving a decreased volume and an impaired function of an adipose tissue caused due to the involution of the adipose tissue and giving a synergistic effect to the expression of a skin moisturizing factor.

11 Claims, 3 Drawing Sheets

COSMETIC COMPOSITION COMPRISING AMIDE-BASED COMPOUND

CROSS-REFERENCE TO RELATED APPLICATIONS

This application claims priority under 35 U.S.C. § 119 to Korean Patent Application No. 10-2020-0031120, filed on Mar. 13, 2020, in the Korean Intellectual Property Office, the disclosure of which is incorporated herein by reference in its entirety.

TECHNICAL FIELD

The following disclosure relates to a cosmetic composition including an amide-based compound, and more particularly, to a cosmetic composition for promoting lipid biosynthesis, a cosmetic composition for inducing differentiation of adipose precursor cells or stem cells into adipocytes, and a cosmetic composition for moisturizing the skin, all of which include an amide-based compound.

BACKGROUND

Hypodermic fats located between the dermis and the muscle fascia are connective tissues which include adipocytes, in which body fats are stored, adipose precursor cells, adipose-derived stem cells, blood vessels, neural networks, and the like. The hypodermic fats basically function to store energy, protect body temperature, absorb shock, and the like. Also, the hypodermic fats secrete various hormones, growth factors, cytokines, and the like. Therefore, the hypodermic fats serve to improve the appearance of the skin by regulating the immune system, body temperature, and the growth and aging of the skin tissue. In addition, the hypodermic fats provide elasticity and firmness to the skin, and thus have a huge influence on formation of the individuals' outward appearances.

It is well known that such hypodermic fats generally serve to significantly reduce a volume of the tissue and impair its functions with age. However, an adipose tissue tends to be involuted due to the unbalanced nutrition caused by the excessive diet in modern times even at a relatively young age. This causes problems such as weakened elasticity of the skin caused by a decrease in volume of the adipose tissue and structural collapse of the skin caused by a decrease in strength of the skin, as well as problems such as accelerated aging caused by the malfunction as a skin tissue and an endocrine organ that regulates a systemic metabolism, decreases in immunity and reproductivity, and the like.

To solve these problems, surgical procedure methods such as autologous fat graft surgery using a current invasive method, and the like have been carried out. A method of taking fats from an abdominal or thigh region which is relatively rich in fats and transferring the fats may be used to regenerate a skin depressed by burning, surgery, scars, and the like, or partially improve a decrease in hypodermic fats caused by the aging. However, such a method has drawbacks in that it is very expensive, the autologous adipose tissue has an irregular engraftment rate after the surgical procedure, and this is an invasive method using only a surgical method. Therefore, there is an increasing demand for a non-invasive method capable of recovering the involution of a layer of hypodermic fats while supplementing these drawbacks.

In recent years, a lot of research proved that there are mesenchymal pluripotent stem cells in the hypodermic fats. These stem cells are referred to as adipose tissue-derived stem cells, and are differentiated into mature adipocytes according to environmental signals. Moreover, the stem cells help to maintain the homeostasis of the adipose and skin tissues by secreting various hormones and cytokines. Also, when the adipose-derived stem cells are induced to be differentiated into the hypodermic fats, a non-invasive and stable fat regeneration method having the same or better effect as in the autologous fat graft surgery may be expected.

Also, the epidermis positioned at the outermost layer of the skin has protective functions in offering protection against a variety of the outside physical, chemical, and mechanical stimuli and preventing an excessive emission of fluids in the body through the skin. Such protective functions make it possible to normally form and maintain the stratum corneum composed of keratinocytes. The keratinocytes are cells formed by gradually undergoing a change in shape and function while allowing basal cells, which have continuously grown in the stratum basale, to move toward the stratum corneum. In this case, the keratinocytes repeat an epidermis differentiation or keratinization process in which old keratinocytes are exfoliated from the skin after a predetermined period of time, and new keratinocytes grown from the stratum basale replace that function. In this keratinization process, the keratinocytes produce natural moisturizing factors (NMFs), and intercellular lipids such as ceramides, cholesterols, and fatty acids to allow the stratum corneum to serve as a barrier layer blocking them from the outside, which makes it possible to maintain the functions as a skin barrier.

Further, xeroderma regarded as one of the major disease in the modern society is one of the symptoms that are caused by the dysfunction of the skin barrier, and is gradually increasing with various factors such as recent environmental pollution, an increase in arid environments such as apartments, high-rise buildings, and the like, an increase in social stress, unusual bathing culture peculiar to Korea, skin aging, and the like. Also, cases in which the xeroderma is required to be treated as its symptom becomes severe have continuously increased. Because the prior art focused on proper maintenance of water in the skin, a lot of research have been conducted to supply water from the outside and minimize the water loss from the body. In fact, moisturizing materials having a water retention ability have been widely used.

However, because such a moisturizing agent is mainly used not to basically treat the xeroderma but to temporarily relieve its symptoms, it is true that it does not exert a sufficient effect on improvement of the xeroderma and the skin barrier dysfunction. Accordingly, there is still a need for development of materials that essentially restore the damaged skin barrier function by maintaining moisture and preserving a distribution ratio of lipids and an amount of lipids.

SUMMARY

An embodiment of the present invention is directed to providing a cosmetic composition for promoting expression of filaggrin and loricrin in order to significantly improve the skin barrier dysfunction as well as promote lipid biosynthesis and promote differentiation of adipose precursor cells or stem cells into adipocytes.

In a general aspect, a cosmetic composition for promoting lipid biosynthesis includes N-(2,3-dihydroxypropyl)hexanamide, N-(2-hydroxy-1-(hydroxymethyl)ethyl)decanamide, or a combination thereof as an active ingredient.

In the cosmetic composition according to one embodiment of the present invention, the lipid biosynthesis may be fulfilled in keratinocytes, sebocytes, or the like.

In the cosmetic composition according to one embodiment of the present invention, the promotion of the lipid biosynthesis may be performed by promoting expression of peroxisome proliferator-activated receptor-gamma.

In another general aspect, a cosmetic composition for inducing differentiation of adipose precursor cells or stem cells into adipocytes includes N-(2,3-dihydroxypropyl) hexanamide, N-(2-hydroxy-1-(hydroxymethyl)ethyl)decanamide, or a combination thereof as an active ingredient.

In the cosmetic composition according to one embodiment of the present invention, the stem cells may be stem cells derived from a human adipose tissue.

In the cosmetic composition according to one embodiment of the present invention, the stem cells may be mesenchymal stem cells.

The cosmetic composition according to one embodiment of the present invention may increase expression of peroxisome proliferator-activated receptor gamma.

The cosmetic composition according to one embodiment of the present invention may increase expression of cluster of differentiation 44 (CD44).

In still another general aspect, a cosmetic composition for moisturizing the skin includes N-(2,3-dihydroxypropyl) hexanamide, N-(2-hydroxy-1-(hydroxymethyl)ethyl)decanamide, or a combination thereof as an active ingredient.

The cosmetic composition according to one embodiment of the present invention may increase a skin moisturizing factor.

In the cosmetic composition according to one embodiment of the present invention, the skin moisturizing factor may be selected from filaggrin and loricrin.

In the cosmetic composition according to one embodiment of the present invention, the active ingredient may be included at 0.001 to 5% by weight, based on the total weight of the cosmetic composition.

The cosmetic composition according to one embodiment of the present invention may be formulated into a lotion, a toner, a face lotion, an eye cream, a nourishing cream, a massage cream, a cleansing cream, a cleansing foam, a cleansing water, an essence, a pack, or the like.

In yet another general aspect, a method for improving skin conditions using, as cosmetics, a composition including N-(2,3-dihydroxypropyl)hexanamide, N-(2-hydroxy-1-(hydroxymethyl)ethyl)decanamide, or a combination thereof as an active ingredient is provided.

In the method according to one embodiment of the present invention, improvement may be achieved by increasing expression of peroxisome proliferator-activated receptor gamma; increasing expression of cluster of differentiation 44; and increasing a skin moisturizing factor.

DETAILED DESCRIPTION OF EMBODIMENTS

Figure 1:
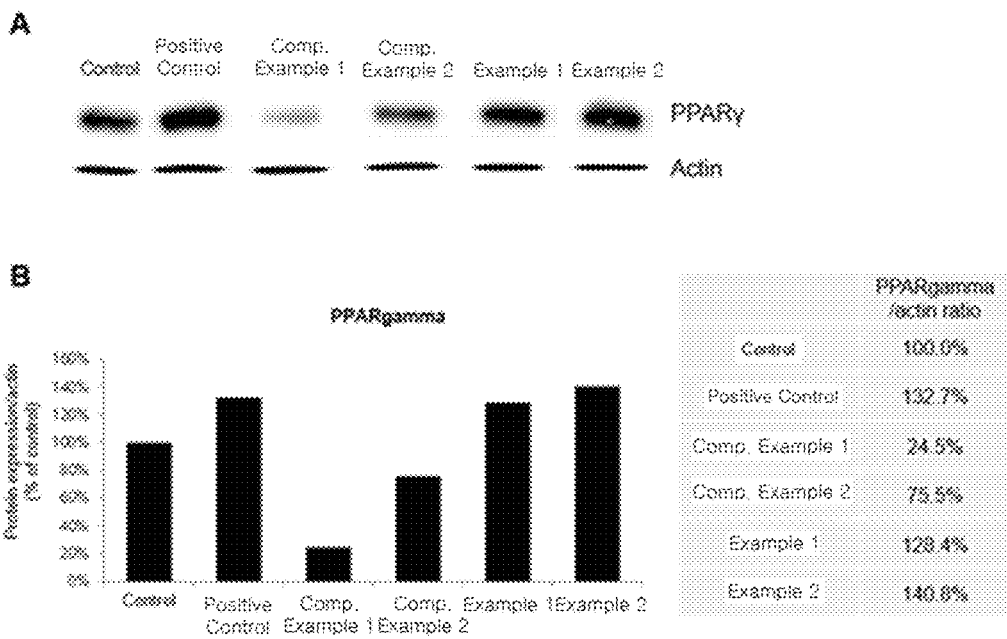
FIG. 1 is a graph showing PPAR-γ expression-promoting effects in sebocytes treated with each of samples of Examples and Comparative Examples of the present invention, compared to those of the control and the positive control.

Hereinafter, a cosmetic composition including an amide-based compound according to the present invention will be described in detail. In this case, unless otherwise defined, the technical and scientific terms used herein have the same meaning as commonly understood by one of ordinary skill in the art to which the present invention pertains. In the following description, a description of known functions and configurations, which may unnecessarily obscure the subject matter of the present invention, will be omitted.

The term "precursor cell" used in this specification is referred to as a committed stem cell. When cells (X) corresponding to a progeny are identified to express a differentiation trait, undifferentiated parent cells in which the differentiation trait is not expressed are referred to as precursor cells of X. Also, the term "adipose precursor cell" refers to a precursor cell that is identified to express a differentiation trait into adipocytes.

The term "stem cell" used in this specification refers to an undifferentiated cell of an animal, and also refers to a cell that exists in all multicellular organisms, and has a self-renewal ability to proliferate indefinitely and an ability to maintain normal chromosomes and differentiate into various cells. The stem cells are known to be master cells in the body due to their totipotent potential which allows them to differentiate into cells of any tissues that constitute 210 organs in the body. One example of these stem cells may include embryonic stem cells, adult stem cells, cord blood stem cells, mesenchymal stem cells, human adipose tissue-derived stem cells, or the like according to what the stem cells are derived from. More specifically, in this specification, the stem cells may be mesenchymal stem cells or adipose tissue-derived mesenchymal stem cells.

The term "mesenchymal stem cell" used in this specification is a mesenchymal stem cell that differentiates into mesenchymal tissues such as muscles, bone, lipids, and the like, and thus refers to one of the adult stem cells (AS) that exists in the bone marrow and has an ability to differentiate into cells such as nerves, skin, and the like. Such adult stem cells are found in organs which repeatedly undergo continuous cell replacement. In this case, these organs may include an outer layer of the skin, an inner membrane of the small intestine, bone marrow, brain, tendon, and the like.

The term "adipose tissue-derived stem cell" used in this specification refers to a cell that is distributed in the adipose tissue and has pluripotency. It is reported that they have a level of differentiation potential equivalent to the bone marrow mesenchymal stem cells, and are superior to the bone marrow mesenchymal stem cells in maintaining a colony forming ability and a proliferation ability in the cell culture. Also, it is known that the proliferation of the adipose tissue-derived stem cells may be stimulated by fibroblast growth factor 2 (FGF-2), and the adipocyte-derived stem cells secrete potential growth factors such as a vascular endothelial growth factor (VEGF), a hepatocyte growth factor (HGF), an insulin-like growth factor (IGF), and the like. The adipose tissue-derived stem cells have advantages in that they may be repeatedly taken several times unlike the stem cells isolated from the bone marrow or the cord blood, and no pain is inflicted on patients when they are taken from the bone marrow, and also has an advantage in that they have no immunological rejection response because they are mainly autologous.

The term "differentiation into adipocytes" used in this specification means that adipose precursor cells or stem cells of an animal, specifically, a mammal, differentiate into adipocytes. The term "composition for inducing differentiation" used in this specification refers to a composition that can induce a process of allowing cells at an early stage to gain the natures of each of tissues. For the purpose of the present invention, the composition for inducing differentiation refers to a composition that can induce differentiation of the adipose precursor cells or stem cells into adipocytes.

The term "peroxisome proliferator-activated receptor gamma (PPAR-$\gamma$)" used in this specification is known as a glitazone receptor or NR1C3 (nuclear receptor subfamily 1, group C, member 3), and is a type II nuclear receptor that is encoded by a PPARG gene and exists in human beings. The PPAR-$\gamma$ is a master regulator for lipid differentiation, and thus may be used as an adipocyte differentiation marker capable of determining a degree of differentiation of the adipose tissue-derived stem cells into adipocytes.

The term "CD44" used in this specification refers to cluster of differentiation 44 that is a marker for labeling adipose tissue-derived stem cells. Here, an increase in expression level of the CD44 means that the activity of the adipose tissue-derived stem cells increases.

The term "filaggrin" used in this specification refers to a keratin binding protein that is isolated from mammalian epidermal cells, that is, a basic protein having a molecular weight of approximately 260,000. In this case, it is known that the protein binds to a keratin unit at a ratio of approximately 3:2 to form fibers, the fibers are aggregated in the form of bundles to form macrofibrils, and the macrofibrils undergo cleavage by a protease enzyme and dephosphorylation to form filaggrin when they are accumulated in the cells to differentiate as a highly phosphorylated precursor having a molecular weight of approximately 500,000.

The term "loricrin" used in this specification is expressed while undergoing a final differentiation. In this case, the loricrin binds to a cell membrane at a supragranular layer to complete a protein. Therefore, the loricrin may be used as a marker in tracking a final differentiation process of keratinocytes.

The present inventors have repeatedly conducted research on cosmetic materials, and confirmed that an amide-based compound having a certain structure may regulate expression of peroxisome proliferator-activated receptor gamma (PPAR-$\gamma$). Also, the present inventors have found that compounds having similar structural characteristics also exhibit a non-specific effect, and further conducted the research.

In particular, the present inventors have focused on N-(2,3-dihydroxypropyl)hexanamide and N-(2-hydroxy-1-(hydroxymethyl)ethyl)decanamide. The aforementioned amide-based compounds promote the expression of PPAR-$\gamma$ and simultaneously exert a significant effect in inducing the differentiation of adipose precursor cells or stem cells into adipocytes. Also, the amide-based compounds have a synergy in supplementing and maintaining various skin moisturizing factors and an amount of lipids. Accordingly, the present inventors have found their use, which has not been known in the prior art, based on such effects, and thus tried to propose the present invention.

Hereinafter, the present invention will be described in detail.

A cosmetic composition of the present invention includes N-(2,3-dihydroxypropyl)hexanamide, N-(2-hydroxy-1-(hydroxymethyl)ethyl)decanamide, or a combination thereof as an active ingredient, and thus its specific functions are as follows.

A first aspect of the present invention is a cosmetic composition for promoting lipid biosynthesis.

The cosmetic composition for promoting lipid biosynthesis according to the present invention i) promotes expression of PPAR-$\gamma$, and ii) promotes differentiation of sebocytes. Therefore, the cosmetic composition of the present invention may improve the collapse of homeostasis of epidermal lipids of the skin.

In the cosmetic composition for promoting lipid biosynthesis according to one embodiment of the present invention, the lipid biosynthesis may be fulfilled in keratinocytes or sebocytes, and may be fulfilled by promoting the expression of PPAR-$\gamma$ in the cells as described above.

The cosmetic composition for promoting lipid biosynthesis according to the present invention induces an increase in an amount of lipids and increases induction of synthesis of lipids in keratinocytes. Also, the cosmetic composition promotes the synthesis of triglycerides to give a synergy to its effect.

A second aspect of the present invention is a cosmetic composition for inducing differentiation of adipose precursor cells or stem cells into adipocytes.

The cosmetic composition for inducing differentiation of adipose precursor cells or stem cells into adipocytes according to the present invention i) promotes expression of PPAR-$\gamma$, ii) increases adipocytes, and iii) increases expression of cluster of differentiation 44. Therefore, the cosmetic composition of the present invention may promote the differentiation of adipose tissue-derived stem cells into mature adipocytes, thereby improving the skin problems caused by the decreased volume and impaired function of an adipose tissue due to the involution of the adipose tissue.

In the cosmetic composition for inducing differentiation of adipose precursor cells or stem cells into adipocytes according to one embodiment of the present invention, the stem cells may be specifically human adipose tissue-derived stem cells, and may be more specifically mesenchymal stem cells.

A third aspect of the present invention is a cosmetic composition for moisturizing the skin.

The cosmetic composition for moisturizing the skin according to the present invention promotes expression of skin moisturizing factors such as filaggrin, loricrin, and the like to significantly improve an ability of the skin tissue to maintain water when applied to the skin, and enhances a skin barrier to give a synergy to its effect.

The cosmetic composition of the present invention may relax and improve a volume of the involuted adipose tissue by simultaneous achievement of the effects as described above. Therefore, because it is suggested that the cosmetic composition of the present invention may help a damaged skin to restore its original function in addition to the skin regeneration, the cosmetic composition of the present invention may be used for skin regeneration.

Also, the present invention may be used as a use of a method of applying the aforementioned cosmetic composition of the present invention to the skin to improve skin conditions. The improvement may be achieved from one or more effects selected from the group consisting of an increase in expression of peroxisome proliferator-activated receptor gamma; an increase in expression of cluster of differentiation 44; and an increase in a skin moisturizing factor.

As described above, the cosmetic composition of the present invention is characterized by including, as an active ingredient, an amide-based compound selected from N-(2,3-dihydroxypropyl)hexanamide, N-(2-hydroxy-1-(hydroxymethyl)ethyl)decanamide, and a combination thereof, and the amide-based compound has the following structure.

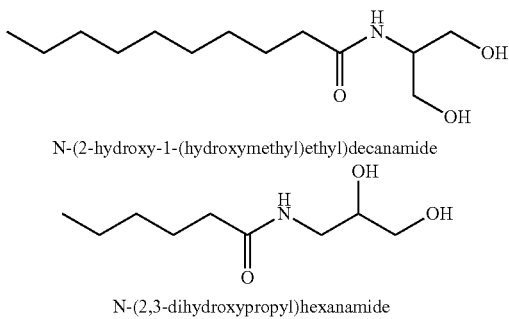

N-(2-hydroxy-1-(hydroxymethyl)ethyl)decanamide

N-(2,3-dihydroxypropyl)hexanamide

As one example, the cosmetic composition of the present invention may also include a pharmaceutically acceptable salt of the amide-based compound or a solvate and stereoisomer thereof as the active ingredient according to one aspect of the present invention.

The amide-based compound may be used safely because the amide-based compound does not cause cytotoxicity and skin stimulation when used in an amount that exerts a significant effect on the skin. Also, the amide-based compound may stably maintain its effect in a formulation and does not cause a phenomenon in which it is not precipitated or separated in the formulation, and also has good storage stability as well.

In the cosmetic composition according to one embodiment of the present invention, the active ingredient may be included at 0.001 to 5% by weight, based on the total weight of the cosmetic composition. Specifically, the active ingredient may be included at 0.001 to 3% by weight, and more specifically 0.01 to 1% by weight. When the active ingredient is included in this range, the cosmetic composition of the present invention has an effect (i.e., a significant use) required in the present invention without impairing the stability of the formulation, which is more preferable.

Also, in the cosmetic composition according to one embodiment of the present invention, when the active ingredient is included as one aspect of a mixture, the active ingredient may give a more significant synergy, which is more preferable. In particular, when the combination of N-(2,3-dihydroxypropyl)hexanamide and N-(2-hydroxy-1-(hydroxymethyl)ethyl)decanamide is included as the active ingredient, the combination exhibits significance in promoting the expression of the skin moisturizing factor.

As one example, when the mixed active ingredients (at a weight ratio of 1:1) are included, the mixed active ingredients exhibit a synergistic effect, compared to when the same amount of the single ingredient used is included.

As one example, in the case, of the mixed active ingredients, the N-(2,3-dihydroxypropyl)hexanamide and the N-(2-hydroxy-1-(hydroxymethyl)ethyl)decanamide may be mixed at a weight ratio of 0.01:99.99 to 99.99:0.01, and may be specifically mixed at a weight ratio of 1:9 to 9:1, and more specifically a weight ratio of 1:1 to 9:1, but the present invention is not limited thereto.

The cosmetic composition according to one embodiment of the present invention may include the aforementioned active ingredient and the balance of water. In this case, it is true that the cosmetic composition according to one embodiment of the present invention may be formulated into various aspects.

The cosmetic composition according to one embodiment of the present invention may be formulated into general emulsion formulations, solubilization formulations, and the like using a preparation method commonly known in the art.

As one example, the cosmetic composition may be formulated into a formulation selected from a lotion, a toner, a face lotion, an eye cream, a nourishing cream, a massage cream, a cleansing cream, a cleansing foam, a cleansing water, an essence, a pack, and the like, but the present invention is not limited thereto.

Also, the cosmetic composition may further properly include an additional additive according to a purpose. In addition to the amide-based compound, the cosmetic composition may further include a component selected from an anti-wrinkle component, an antioxidant component, a whitening component, and the like, all of which are known in the art. As one example, the additional additive may be selected from retinoic acid, TGF, an animal placenta-derived protein, betulinic acid, a chlorella extract, and the like, but the present invention is not limited thereto.

In addition, the cosmetic composition may further include one or more additives selected from one or more aqueous additives selected from a stabilizing agent, an emulsifying agent, a thickening agent, a moisturizing agent, a liquid crystal film-enhancing agent, a pH regulating agent, an antibacterial agent, a water-soluble polymer, a film-forming agent, a metal ion-sequestering agent, an amino acid, an organic amine, a polymer emulsion, a pH adjusting agent, a skin nutrient, an antioxidant, an antioxidative aid, a preservative, a fragrance, and the like; and one or more oily additives selected from fat and oils, waxes, a hydrocarbon oil, a high-grade fatty acid oil, a higher alcohol, a synthetic ester oil, a silicone oil, and the like.

In this case, each of the additives may be included at 0.001 to 20% by weight, specifically 0.01 to 101 by weight, and more specifically 0.05 to 5% by weight, based on the total weight of the cosmetic composition, but the present invention is not limited thereto.

(Evaluation Method)

1. Analysis of Expression Level of PPAR-γ

An expression level of PPAR-γ was determined through Western blot in Examples and Comparative Examples of the present invention.

Specifically, human sebocytes were cultured in a 12-well plate containing a Dulbecco's modified eagle medium (DMEM)/F12 (1:1) medium supplemented with 10% fetal bovine serum (FBS) to attach $1.5 \times 10^5$ (1 mL/well) sebocytes to the 12-well plate. The sebocytes were cultured for 24 hours, and the medium was replaced with a serum-free medium. Then, an experimental group in which the cells were treated with each of the compounds of Examples or Comparative Examples was cultured for 24 hours, and the cells were then recovered. Thereafter, each of these samples was subjected to Western blot to analyze an expression level of PPAR-γ in the sebocytes. A sample (100 μM) of Example 1 or 2 or Comparative Example 1 or 2 including the amide-based compound having a structure shown in the following Table 1 was used as the sample. Also, a sample treated with 10 μM IGF-1 was used as the positive control, and the control in which the cells were not treated with the sample was used as the comparison group.

The results thus obtained are shown in FIG. 1 below.

2. Confirmation of Effect of Inducing Differentiation into Adipocytes $1 \times 10^5$=(1 mL/well) sebocytes were attached to a 12-well plate containing a medium supplemented with human sebocytes in the same manner as in the Evaluation Method of Section 1, and cultured for 24 hours. Thereafter, the medium was replaced with a 1, fetal bovine serum medium. Thereafter, an experimental group in which the cells were treated with each of the compounds of Examples or Comparative Examples was cultured for 48 hours. The cells were stained with a Nile red (1 μg/mL) solution for 30 minutes. Then, a cover slide attached to the stained cells was covered with a slide on which one drop of a mounting solution was placed, set completely, and then observed on a microscopic image.

Figure 2:
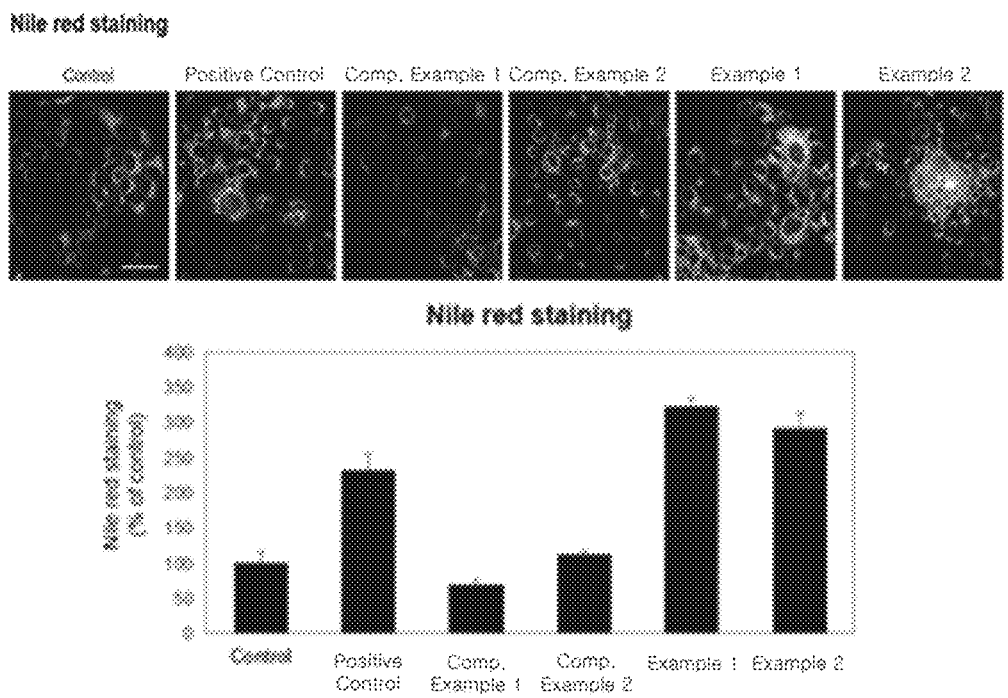
FIG. 2 is a microscopic image of staining the sebocytes treated with each of the samples of Examples and Comparative Examples of the present invention with a Nile Red reagent to compare fluorescence intensities in the sebocytes, compared to those of the control and the positive control.

The results thus obtained are shown in FIG. 2 below.

3. Analysis of Expression Level of CD44

For flow cytometric analysis of the adipose tissue-derived stem cells of Examples and Comparative Examples of the present invention, an expression level of CD44 was measured. For this purpose, each of the samples was added to each medium. A sample (100 μM) of Example 1 or 2 or Comparative Example 1 or 2 including the amide-based compound having a structure shown in the following Table 1. Also, a sample treated with 10 μM IGF-1 was used as the positive control, and the control in which the cells were not treated with the sample was used as the comparison group.

Specifically, RNA was isolated from human adipose tissue-derived mesenchymal stem cells (hADSCs) according to the manufacturer's instructions using an easy BLUE reagent. The isolated RNA was dissolved in distilled water supplemented with diethyl procarbonate (DEPC), and the absorbance was measured at 260 nm, and a concentration of the RNA was quantified, and then used for experiments. Then, an expression level of CD44 in the adipose tissue-derived stem cells was analyzed.

Figure 3:
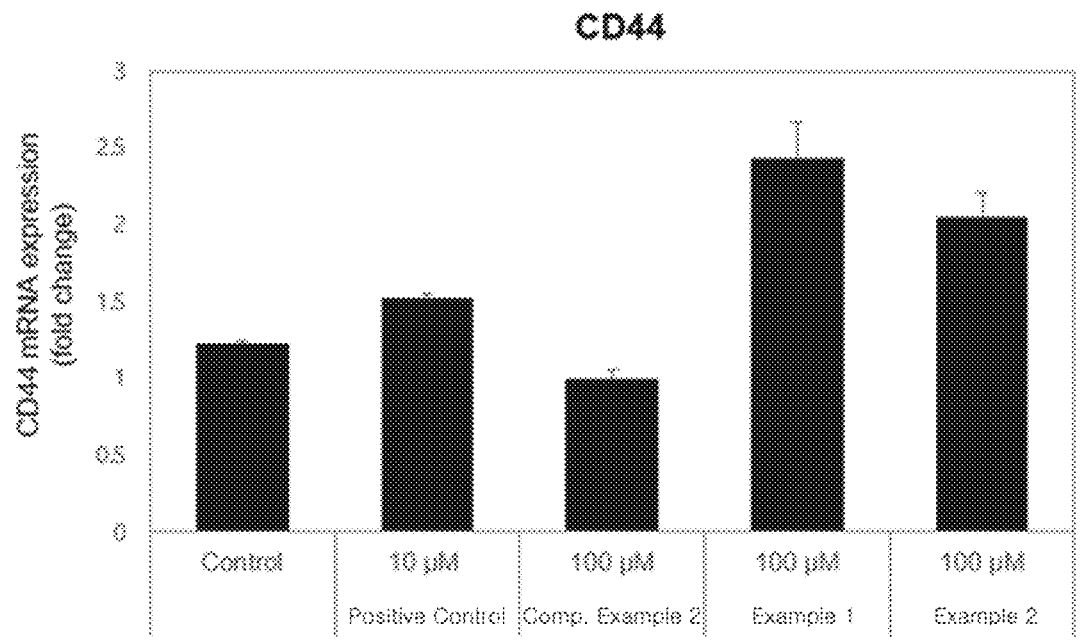
FIG. 3 is a graph showing an expression level of CD44, compared to those of the control and the positive control, after adipose tissue-derived mesenchymal stem cells are treated with each of the samples of Examples and Comparative Examples of the present invention.

The results thus obtained are shown in FIG. 3 below.

4. Analysis of Expression Levels of Filaggrin and Loricrin

To determine effects of the samples of Examples and Comparative Examples of the present invention on promotion of expression of moisturizing factors, expression levels of filaggrin and loricrin were measured.

Specifically, keratinocytes commercially available from Invitrogen Corp. were cultured for a predetermined period of time in an EpiLife medium (keratinocyte growth media: keratinocyte growth medium) supplemented with a human keratinocyte growth supplement (HKGS), subcultured three times, and then used. The keratinocytes which were subcultured 3 times were cultured to a confluence of 70 to 80% in a 6-well plate, and each of the wells was separately treated with each of the samples. Thereafter, the cells were cultured for a total of 24 hours. RNA of the keratinocytes was extracted from the cultured cells using an easy BLUE reagent, and cDNA was synthesized using a SuperScript reverse transcriptase III kit. A 7500 Fast Real-Time PCR for genetic comparison was performed using a 2×TaqMan universal PCR mixture (10 μL), a 20×TaqMan expression assay mix (1 μL), cDNA (50 ng), and primers (Filaggrin: Hs00856927_g1*, Loricrin: Hs01894962_s1*). Also, a sample treated with 10 μM IGF-1 was used as the positive control, and the control in which the cells were not treated with the sample was used as the comparison group.

Figure 4:
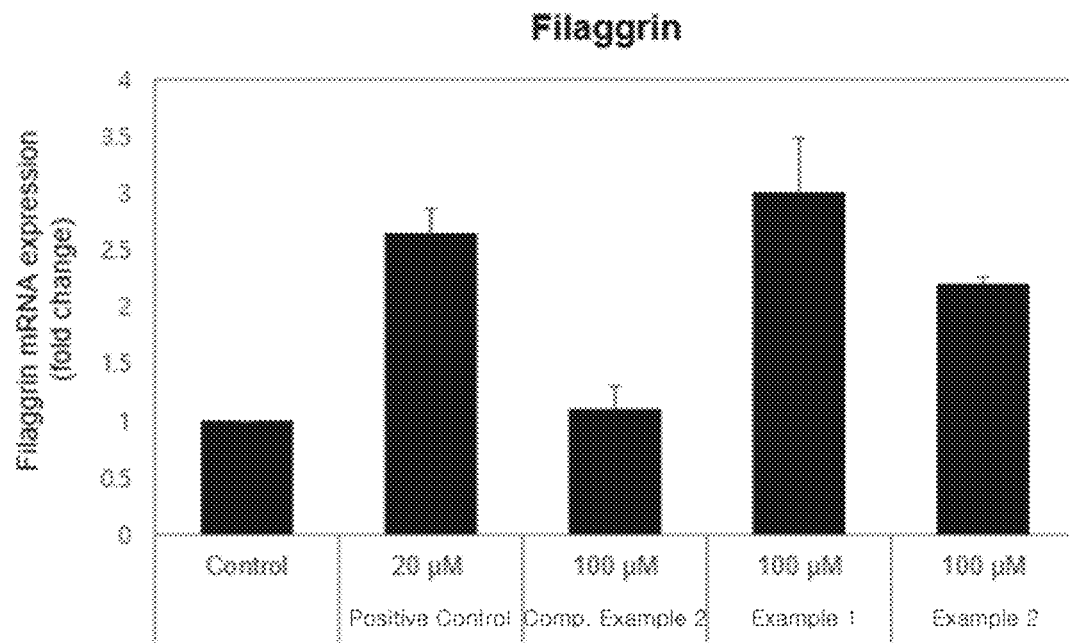
FIG. 4 is a graph showing the results of expression of a filaggrin gene, compared to those of the control and the positive control, after the stem cells are treated with each of the samples of Examples and Comparative Examples of the present invention.
Figure 5:
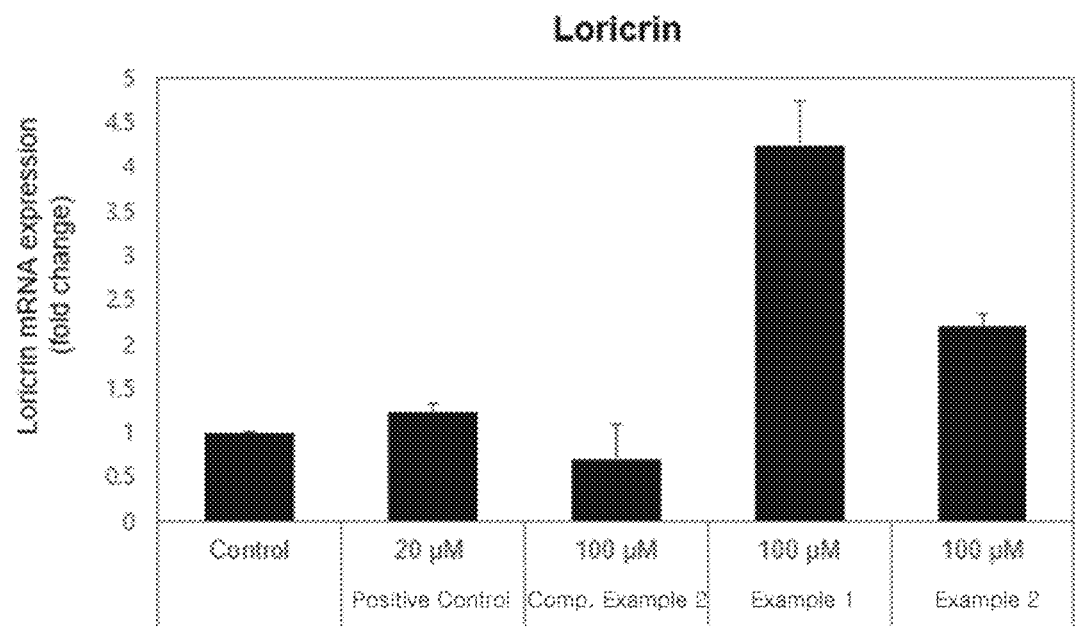
FIG. 5 is a graph showing the results of expression of a loricrin gene, compared to those of the control and the positive control, after the stem cells are treated with each of the samples of Examples and Comparative Examples of the present invention.

The results thus obtained are shown in FIGS. 4 and 5 below.

Examples 1 and 2

The evaluation method was performed using the amide-based compounds having a structure shown in the following Table 1. The sample of each of Examples was prepared at a concentration of 100 μM.

Comparative Examples 1 and 2

The evaluation method was performed using the amide-based compounds having a structure shown in the following Table 1. The sample of each of Comparative Examples was prepared at a concentration of 100 μM.

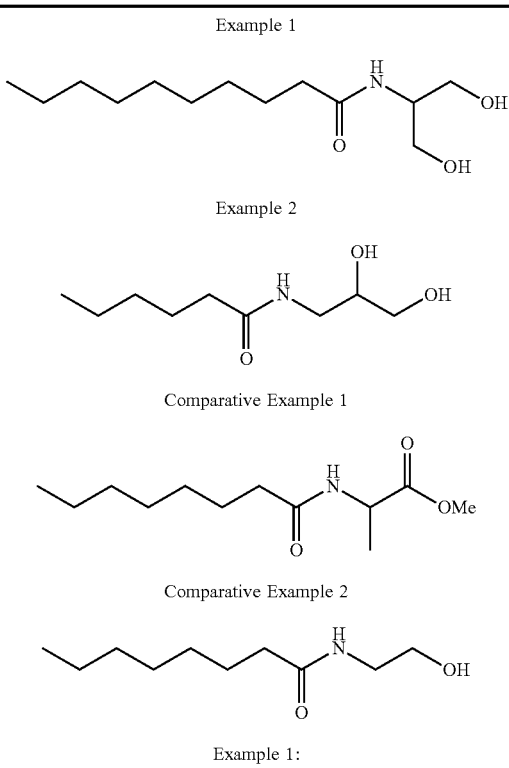

Example 1:
N-(2-hydroxy-1-(hydroxymethyl)ethyl)decanamide
Example 2:
N-(2,3-dihydroxypropyl)hexanamide
Comparative Example 1: 4-heptylidene-3-hexyloxetan-2-one
Comparative Example 2: N-(2-hydroxyethyl)octanamide As shown in FIGS. 1 and 2 below, it was confirmed that the expression of PPAR-γ was promoted by the samples treated with IGF-1 (positive control) and the samples treated with the compounds of the present invention (Examples). Specifically, it was confirmed that the samples treated with the compound of Example 1 or 2 of the present invention exhibited an effect of improving the expression of PPAR-γ by 128.4, or 140.8%, respectively.

On the other hand, the samples treated with the compound of Comparative Example 1 or 2 whose structural characteristics were similar to those of the compounds of the present invention had a phenomenon in which they did not promote the expression of PPAR-γ but inhibited the expression of PPAR-γ. Specifically, it was confirmed that the samples treated with the compound of Comparative Example 1 or 2 inhibited the expression of PPAR-γ by 24.5% or 75.5%, compared to the control.

As shown in FIGS. 1 and 2 below, it was confirmed that the samples treated with the compounds of the present invention induced the differentiation of the sebocytes more effectively in a concentration-dependent manner. As a result, it was confirmed that the samples treated with the compounds of the present invention increased the lipid biosynthesis to increase generation of lipid bubbles when stained with a Nile red reagent.

As shown in FIG. 3 below, it was confirmed that the samples treated with the compounds of the present invention significantly increased an expression level of CD44 by 200% or more, compared to the control. Such an effect on an increase in the expression level of CD44 means an increase in activity of the adipose tissue-derived stem cells. Accordingly, according to the present invention, the amide-based compounds were able to promote the differentiation into the adipocytes to maximize effects of skin regeneration and wound healing. On the other hand, the sample treated with the compound of Comparative Example 2 did not have an effect of significantly promoting an expression level of CD44, and exhibited a lower expression level of CD44, compared to the control.

As shown in FIGS. 4 and 5 below, it was confirmed that all the samples treated with the compounds of the present invention promoted the expression of filaggrin and loricrin. In particular, it was confirmed that the samples treated with the compound of Example 1 had enhanced expression levels of filaggrin and loricrin by 300% or more and 400% or more, respectively, compared to the control. Also, it was confirmed that all the samples treated with the compounds of the present invention had increased expression levels of filaggrin and loricrin, indicating that this effect was achieved as a remarkably improved effect, compared to the sample treated with the compound of Comparative Example 2.

According to the present invention, the cosmetic composition can promote the lipid biosynthesis, and can simultaneously promote the differentiation of adipose tissue-derived stem cells into mature adipocytes by promoting the expression of cluster of differentiation 44 and PPAR-γ, which is a master regulator for lipid differentiation and is a marker for labeling human adipose tissue-derived stem cells, thereby providing a novel use that can improve the aesthetic and health problems of modern people caused by the decreased volume and impaired function of the adipose tissue due to the involution of the adipose tissue.

When the cosmetic composition of the present invention is applied onto the human body, the cosmetic composition of the present invention can promote expression of a skin moisturizing factor to aid in stably maintaining water in the skin tissue and enhance the skin barrier, and thus can have an excellent skin moisturizing effect of maintaining water in the skin. Also, the cosmetic composition of the present invention is safe for the human body, and had no side effects when used for a long period of time.

Hereinabove, although the present invention has been described with reference to the specific subject matters and limited embodiments thereof, they have been provided only for assisting in the entire understanding of the present invention. Therefore, the present invention is not limited to the exemplary embodiments. Various modifications and changes may be made from this description by those skilled in the art to which the present invention pertains.

Therefore, the spirit of the present invention should not be limited to the embodiments as described herein, and the following claims as well as all modifications equal or equivalent to the claims are intended to fall within the scope and spirit of the invention.

What is claimed is:

1. A method for improving skin conditions comprising the step of administering to a subject a composition comprising N-(2,3-dihydroxypropyl) hexanamide, N-(2-hydroxy-1-(hydroxymethyl)ethyl)decanamide, or a combination thereof as an active ingredient.

2. The method of claim 1, wherein the improvement is achieved from promoting lipid biosynthesis in keratinocytes or sebocytes; inducing differentiation of adipose precursor cells or stem cells into adipocytes, or moisturizing the skin.

3. The method of claim 2, wherein the promotion of the lipid biosynthesis is performed by promoting expression of peroxisome proliferator-activated receptor-gamma.

4. The method of claim 2, wherein the stem cells are stem cells derived from a human adipose tissue.

5. The method of claim 2, wherein the stem cells are mesenchymal stem cells.

6. The method of claim 2, wherein inducement of differentiation of adipose precursor cells or stem cells into adipocytes is performed by promoting expression of cluster of differentiation 44.

7. The method of claim 2, wherein the moisturizing the skin is achieved by increasing a skin moisturizing factor.

8. The method of claim 7, wherein the skin moisturizing factor is selected from filaggrin and loricrin.

9. The method of claim 1, wherein the active ingredient is included at 0.001 to 5% by weight, based on the total weight of the composition.

10. The method of claim 1, wherein the composition is formulated into a lotion, a toner, a face lotion, an eye cream, a nourishing cream, a massage cream, a cleansing cream, a cleansing foam, a cleansing water, an essence, or a pack.

11. The method of claim 1, wherein the improvement of skin conditions are selected from skin barrier enhancement, skin moisturizing, skin regeneration, or wound healing.

* * * * *